United States Patent
Kosynkin et al.

(10) Patent No.: US 10,620,183 B2
(45) Date of Patent: *Apr. 14, 2020

(54) SYSTEMS AND METHODS FOR REAL-TIME SPECTROPHOTOMETRIC QUANTIFICATION OF CRUDE OIL

(71) Applicant: Saudi Arabian Oil Company, Dhahran (SA)

(72) Inventors: Dmitry Kosynkin, Dhahran (SA); Mohammed Alaskar, Dhahran (SA)

(73) Assignee: Saudi Arabian Oil Company (SA)

(*) Notice: Subject to any disclaimer, the term of this patent is extended or adjusted under 35 U.S.C. 154(b) by 0 days.

This patent is subject to a terminal disclaimer.

(21) Appl. No.: 16/259,780

(22) Filed: Jan. 28, 2019

(65) Prior Publication Data
US 2019/0154650 A1 May 23, 2019

Related U.S. Application Data

(63) Continuation of application No. 15/454,979, filed on Mar. 9, 2017, now Pat. No. 10,324,077.

(51) Int. Cl.
*G01J 3/42* (2006.01)
*G01N 33/28* (2006.01)
(Continued)

(52) U.S. Cl.
CPC ......... *G01N 33/2823* (2013.01); *G01N 21/31* (2013.01); *G01N 21/33* (2013.01);
(Continued)

(58) Field of Classification Search
CPC .. G01N 33/2823; G01N 33/241; G01N 21/31; G01N 21/33; G01N 21/645;
(Continued)

(56) References Cited

U.S. PATENT DOCUMENTS 2,527,121 A 10/1950 Dudenbostel, Jr.
2,767,320 A 10/1956 Coggeshall et al.
(Continued)

FOREIGN PATENT DOCUMENTS

| DE | 102015104531 A1 | 9/2016 |
|---|---|---|
| WO | 2007089154 A1 | 8/2007 |
| WO | 2016105391 A1 | 6/2016 |

OTHER PUBLICATIONS

International Search Report and Written Opinion for related PCT application PCT/US2014/046817, dated Oct. 31, 2014.
(Continued)

*Primary Examiner* — Tarifur R Chowdhury
*Assistant Examiner* — Jonathon Cook
(74) *Attorney, Agent, or Firm* — Bracewell LLP; Constance G. Rhebergen

(57) ABSTRACT

Systems, apparatuses, and computer-implemented methods are provided for the real-time quantification of crude oil in an effluent from coreflooding apparatus. Disclosed here is a method of determining the amount of crude oil in an effluent from a coreflooding apparatus by blending the effluent stream with a solvent stream in a mixing device to produce a mixed stream, supplying the mixed stream to an in-line phase separator to produce a first stream containing the solvent and the crude oil from the effluent stream and a second stream containing water and water-miscible components from the effluent stream; and passing the first stream to a continuous flow spectrophotometer to determine the amount of crude oil in the effluent stream.

26 Claims, 8 Drawing Sheets

(51) Int. Cl.

| | |
|---|---|
| *G01N 33/24* | (2006.01) |
| *G01N 21/31* | (2006.01) |
| *G01N 21/85* | (2006.01) |
| *G01N 21/33* | (2006.01) |
| *G01N 21/64* | (2006.01) |
| *G01N 1/38* | (2006.01) |
| *G01N 35/00* | (2006.01) |
| *G01N 1/40* | (2006.01) |
| *G01N 21/35* | (2014.01) |

(52) U.S. Cl.
CPC .......... *G01N 21/645* (2013.01); *G01N 21/85* (2013.01); *G01N 33/241* (2013.01); *G01N 1/38* (2013.01); *G01N 21/643* (2013.01); *G01N 35/00* (2013.01); *G01N 2001/4061* (2013.01); *G01N 2021/3595* (2013.01)

(58) Field of Classification Search
CPC ........ G01N 21/85; G01N 21/643; G01N 1/38; G01N 35/00; G01N 35/08; G01N 35/1095; G01N 2035/00465; G01N 2001/4061; G01N 2021/3595; G01J 3/02; G01J 3/42
USPC .......................................................... 356/319
See application file for complete search history.

(56) References Cited

U.S. PATENT DOCUMENTS

| | | | |
|---|---|---|---|
| 3,468,789 | A | 9/1969 | Balassa |
| 4,045,671 | A | 8/1977 | Dille et al. |
| 4,146,799 | A | 3/1979 | Pitt et al. |
| 4,313,086 | A * | 1/1982 | Baum ................ G01N 33/1833 324/439 |
| 5,076,909 | A | 12/1991 | Overfield et al. |
| 5,266,800 | A | 11/1993 | Mullins |
| 5,272,346 | A | 12/1993 | Kaplan et al. |
| 5,301,536 | A | 4/1994 | Ortega et al. |
| 5,304,807 | A | 4/1994 | Lin |
| 5,331,156 | A | 7/1994 | Hines |
| 5,561,065 | A | 10/1996 | Schabron |
| 5,679,574 | A | 10/1997 | Friedman et al. |
| 6,117,682 | A | 9/2000 | Lynn et al. |
| 6,794,864 | B2 | 9/2004 | Mirotchnik et al. |
| 6,946,837 | B2 | 9/2005 | Sorland |
| 7,403,292 | B2 | 7/2008 | Tomaru |
| 7,482,811 | B2 | 1/2009 | Freedman |
| 9,297,747 | B2 | 3/2016 | Han et al. |
| 10,031,121 | B2 * | 7/2018 | Koseoglu ............ G01N 33/2823 |
| 2011/0056271 | A1 * | 3/2011 | Larter ................. G01N 33/2823 73/23.37 |
| 2011/0194105 | A1 | 8/2011 | Lafrancois et al. |
| 2013/0125630 | A1 | 5/2013 | Collins et al. |
| 2014/0375991 | A1 | 12/2014 | Schneider et al. |
| 2015/0021490 | A1 | 1/2015 | Han et al. |
| 2015/0106034 | A1 | 4/2015 | Koseoglu et al. |
| 2017/0234842 | A1 * | 8/2017 | Reed .................. B01F 13/1016 422/501 |

OTHER PUBLICATIONS

Elraies, K.A., Tan, I.M. and Awang, M., "A New Approach to Low-Cost, High Performance Chemical Flooding System," SPE 133004, SPE Production and Operations Conference and Exhibition, Tunis, Tunisia, Jun. 8-10, 2010, Society of Petroleum Engineers.

International Search Report and Written Opinion for International Application No. PCT/US2018/021643; report dated Jun. 28,2018; 12 pages.

Patel, "Rapid and Convenient Laboratory Method for Extraction and Subsequent Spectrophotometric Determination of Bitumen Content of Bituminous Sands", Analytical Chemistry, 1974, pp. 794-795, vol. 46, No. 6, XP-002731074.

Product Brochure—OCMA-350 Oil Content Analyzer at http://www.horiba.com/process-environmental/products/water-quality-measurement/lab-use/details/ocma-350-oil-content-monitor-356/.

Taber, J.J., Kamath, I.S.K. and Reed, R.L., "Mechanism of Alcohol Displacement of Oil from Porous Media," Society of Petroleum Engineers Journal, Sep. 1961: pp. 195-212.

Torsaeter, O., Boe, R. and Holt, T. "An Experimental Study of the Relationship between Rock Surface Properties, Wettability and Oil Production Characteristics," SCA-9739, International Symposium of SCA, Calgary, Alberta, Canada, Sep. 7-10, 1997.

* cited by examiner

SYSTEMS AND METHODS FOR REAL-TIME SPECTROPHOTOMETRIC QUANTIFICATION OF CRUDE OIL

CROSS-REFERENCE TO RELATED APPLICATION

This application is a continuation application of U.S. application Ser. No. 15/454,979 filed on Mar. 9, 2017.

FIELD

This disclosure relates to methods, apparatuses, and systems generally directed to quantification of oil in oil-containing fluids.

BACKGROUND

The efficiency of improved oil recovery methods is evaluated using coreflooding systems. A coreflood system flows a fluid through a core sample at simulated reservoir conditions and measures flow parameters. Oil recovered from the coreflooding system can be present as a continuous oil phase, a water-in-oil emulsion containing a certain amount of water and an oil-in-water emulsion containing relatively small, or sometimes trace, amount of oil. The amount of oil from the coreflooding samples is analyzed through a variety of analytical methods to determine the success of oil recovery. These analytical methods include visual observation, infrared spectroscopy, near infra-red reflectance spectroscopy, nuclear magnetic resonance (NMR), and absorption spectroscopy. The cumulative produced oil volumes are determined with high levels of noise and uncertainty by real-time monitoring.

Visual observation involves a sample of the oil-water mixture placed in a graduated cylinder and allowed to separate into an oil phase and a water phase. The amount of oil is then determined based on the height of the oil phase in the graduated cylinder. Visual observation is inaccurate when the amount of oil is less than 0.1 mL. NIR spectroscopy requires a special instrument for the measurement and is sensitive to the changes in the texture of the samples. NMR also requires specialized and expensive equipment for measurement. An OCMA-300 series oil content analyzer can be used for measuring the oil content in emulsion samples. These methods all suffer from major drawbacks. They require expensive, complicated equipment and skilled operators, which adds to the expense of running a sample. The methods can analyze the emulsion samples, but not other samples with trace amounts of oil in water. These methods consume significant time to obtain results on a given sample. Fraction collection based oil quantification methods are very time consuming and laborious. Current practices involve multiple steps, with each step handled manually, thus making these steps error-prone. Fluid level-based methods of cumulative recovered oil monitoring give noisy data that impede evaluation of temporal aspects of improved oil recovery treatments.

SUMMARY

Several disadvantages were recognized by the inventors and various embodiments of this disclosure were developed to address these shortcomings in the art. Certain embodiments disclosed and described here include the use of real-time continuous extraction of oil from the mixed stream to determine oil content. Certain embodiments include computer-implemented methods of real-time analysis of output streams of coreflooding experiments. One such method of determining the amount of crude oil in an effluent from a coreflooding apparatus includes the steps of: supplying an effluent stream obtained from a coreflooding apparatus to a mixing device, the effluent stream containing crude oil and water; blending the effluent stream with a solvent stream in the mixing device to produce a mixed stream; supplying the mixed stream to an in-line phase separator to produce a first stream containing the solvent and the crude oil from the effluent stream and a second stream containing water and water-miscible components from the effluent stream; and passing the first stream to a continuous flow analyzer to determine the amount of crude oil.

The in-line phase separators can include one or more of a membrane separator, a microfluidic separator, a porous media separator, or a centrifugal separator. The continuous flow analyzer can be a member of the group consisting of an ultraviolet fluorescence analyzer, an infrared fluorescence analyzer, a visible spectrophotometer and an ultraviolet/visible spectrophotometer. In an embodiment, the continuous flow analyzer is a continuous flow spectrophotometer. The solvents used to extract crude oil from effluent stream can be one or more of benzene, toluene, xylenes, ethylbenzene, trimethylbenzenes, ethyl acetate, propyl acetate, methyl propionate, or dichloromethane. In certain embodiments, the solvent is toluene, xylenes, or combinations thereof.

Certain embodiments include computer-implemented methods of determining amount of crude oil in an effluent from a coreflooding apparatus. One such method includes the steps of: supplying an effluent stream obtained from a coreflooding apparatus to a mixing device, the effluent stream containing crude oil and water; blending the effluent stream with a solvent stream in the mixing device to produce a mixed stream; supplying the mixed stream to an in-line phase separator to produce a first stream containing the solvent and the crude oil from the effluent stream and a second stream containing water and water-miscible components from the effluent stream; passing the first stream to a continuous flow spectrophotometer to determine a plurality of absorption values corresponding to the crude oil content in the first stream; and transmitting the plurality of absorption values to a data analysis engine to determine the amount of crude oil in the effluent stream. The method can further include the step of varying the rate of supply of the solvent stream to the mixing device in response to determining the amount of crude oil in the effluent stream. The in-line phase separators can include one or more of a membrane separator, a microfluidic separator, a porous media separator, or a centrifugal separator. The solvents used to extract crude oil from effluent stream can be one or more of benzene, toluene, xylenes, ethylbenzene, trimethylbenzenes, ethyl acetate, propyl acetate, methyl propionate, dichloromethane, or combinations thereof.

Certain embodiments include systems for real-time quantification of crude oil in an effluent from a coreflooding apparatus. One such system includes a coreflooding apparatus; a mixing apparatus in fluid communication with the coreflooding apparatus via an effluent line and with a solvent delivery unit via a solvent line; an in-line phase separator in fluid communication with the mixing apparatus via a mixed stream delivery line; a continuous flow analyzer in fluid communication with the phase separator via an oil-phase line and configured to receive a stream containing the solvent and crude oil via an oil-phase line and to transmit a plurality of absorption values to a data analysis engine; and the data analysis engine including a non-transitory storage medium for storing executable program code, which when executed by a processor, causes the processor to quantify crude oil in an effluent from the coreflooding apparatus in response to receipt of the plurality of absorption values. The in-line phase separators can include one or more of a membrane separator, a microfluidic separator, a porous media separator, or a centrifugal separator. The continuous flow analyzer is a member of the group consisting of an ultraviolet fluorescence analyzer, an infrared fluorescence analyzer, a visible spectrophotometer and an ultraviolet/visible spectrophotometer. The mixing apparatus includes one or more of an agitator, a blender, an impeller, a stirrer, or a propeller.

In certain embodiments, the data analysis engine is communicatively coupled to the solvent delivery unit, and can be configured to vary amount of solvent released from the solvent delivery unit to the mixing apparatus in response to determining the amount of crude oil in the effluent. The data analysis engine can be communicatively coupled to the coreflooding apparatus.

Numerous other aspects, features and benefits of the present disclosure may be made apparent from the following detailed description taken together with the drawing figures. The systems can include less components, more components, or different components depending on desired analysis goals.

BRIEF DESCRIPTION OF THE DRAWINGS

While this disclosure is susceptible to various modifications and alternative forms, specific embodiments are shown by way of example in the drawings and will be described in detail here. The drawings may not be to scale. It should be understood, however, that the drawings and the detailed descriptions thereto are not intended to limit the disclosure to the particular form disclosed, but, to the contrary, the intention is to cover all modifications, equivalents, and alternatives falling within the spirit and scope of the present disclosure as defined by the appended claims.

DETAILED DESCRIPTION

Figure 1:
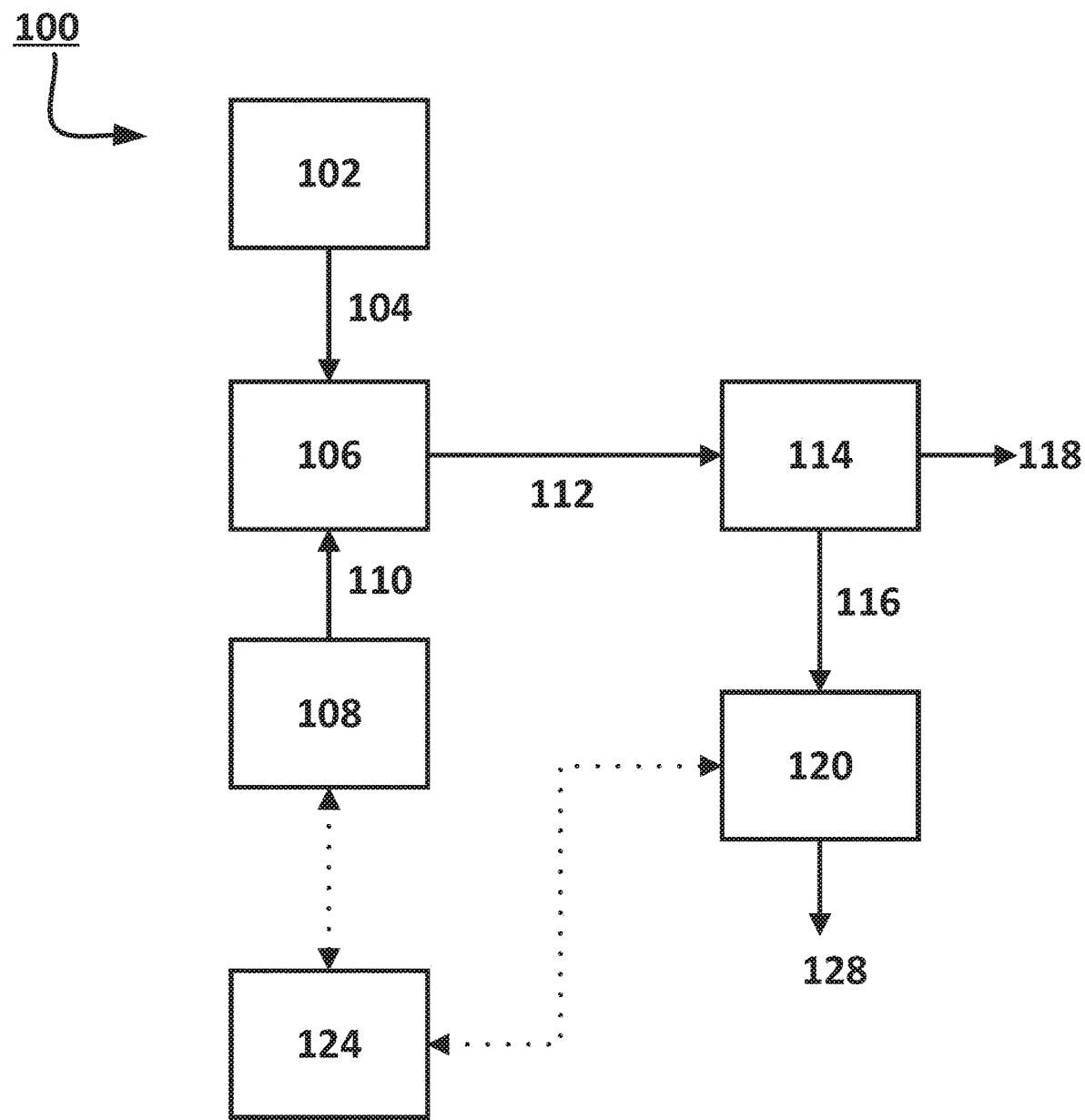
FIG. 1 is an illustration of a system for determining real-time spectrophotometric quantification of crude oil, according to an embodiment.

In the following description, numerous specific details are set forth in order to provide a thorough understanding of the various embodiments. In other instances, well-known processes and methods may not be described in particular detail in order not to unnecessarily obscure the embodiments described here. Additionally, illustrations of embodiments here may omit certain features or details in order to not obscure the embodiments described here.

In the following detailed description, reference is made to the accompanying drawings that form a part of the specification. Other embodiments may be utilized, and logical changes may be made without departing from the scope of the disclosure. Therefore, the following detailed description is not to be taken in a limiting sense.

The description may use the phrases "in some embodiments," "in various embodiments," "in certain embodiment," or "in embodiments," which may each refer to one or more of the same or different embodiments. Furthermore, the terms "comprising," "including," "having," and the like, as used with respect to embodiments of the present disclosure, are synonymous.

Embodiments include methods to determine the amount of crude oil in a fluid stream exiting coreflooding tests using spectrophotometric real-time monitoring. Current methods involve determining an amount of oil either by sending the entire flow to a phase separator equipped with an ultrasonic level gauge or other means of measuring the accumulated volume of oil or by collecting consequent samples of the flow followed by volumetric or spectrophotometric analysis of each sample. The accuracy of volumetric determination of the amount of collected oil can be quite low owing to a tendency of water droplets to remain entrapped in the oil layer for considerable periods of time. Both ultrasonic gauge-mediated and direct visual observation of the oil volume suffer from inability to estimate the volume of entrapped oil droplets.

Disclosed here are systems and methods directed to automated real-time monitoring devices analyzing the effluent streams from coreflooding tests. Certain embodiments of these methods and systems improve the accuracy and reliability of monitoring of real-time cumulative oil production in coreflooding experiments. Embodiments include a method for accurate real-time quantification of the amount of oil in a certain fluid stream containing an aqueous phase, a gaseous phase, or combinations thereof. One such method includes the steps of providing a solvent stream, mixing this solvent stream with the fluid stream to generate a mixed stream, passing the mixed stream through an in-line phase separator to produce a first stream containing the solvent phase with solvent-miscible components and a second stream containing the aqueous phase with water-miscible components. The method further includes sending the first stream to an analytical instrument to determine a concentration of oil in the first stream and integrating the measured concentration values to determine the cumulative amount of oil in the certain stream. In-line phase separators include, but are not limited to, membrane, microfluidic, porous media and centrifugal separators. In certain embodiments, the solvent stream is a precisely controlled stream of a solvent, such as benzene, toluene, xylenes, ethylbenzene, trimethylbenzenes, ethyl acetate, propyl acetate, methyl propionate and dichloromethane. Mixers used in these embodiments include any apparatus used to change a non-uniform system into a uniform one (i.e., the random distribution of two or more initially separated phases). For example, mixers can use agitators, blenders, impellers, stirrers, or propellers to mix the solvent stream and the effluent stream. Analytical equipment include ultraviolet fluorescence analyzer, infrared fluorescence analyzer, and visible and UV/visible spectrophotometers.

FIG. 1 is a block diagram of an analytical system 100. A coreflooding apparatus 102 with at least three main components: the upstream, the core block, and the downstream. The upstream component has pumps, pipes, and injection systems to maintain pressure, volume, and flowrate capabilities and supply fluids to the core block. The core block component usually contains a cylindrical rock cut from the reservoir during a separate core drilling operation or a formation outcrop. The downstream component has effluent collection and flow systems. The effluent line 104 from the coreflooding apparatus supplies an effluent stream to the mixing apparatus 106. A solvent delivery unit 108 delivers a solvent stream via solvent line 110 to the mixing apparatus 106. At this step, the mixing apparatus 106 mixes contents of the effluent stream and the solvent stream to produce a mixed stream that leaves the mixer via mixed stream delivery line 112 to a phase separator 114. In the phase separator 114, this mixed stream is separated to produce two streams, a first stream exiting via an oil-phase line 116 and a second stream exiting via an aqueous line 118. The types of the in-line separators that can be used in these systems include, but are not limited to, membrane, microfluidic, porous media and centrifugal separators. The first stream contains the solvent and solvent-miscible oil components from the effluent stream. The second stream is an aqueous stream and contains the water miscible fraction of the effluent stream. The first stream is supplied via an oil-phase line 116 to a continuous flow spectrophotometer 120 to determine the concentration of oil in the first stream from the spectrophotometric signal. Absorption data from the continuous flow spectrophotometer 120 is communicated to a data analysis engine 124, where it is analyzed to determine the oil content in the effluent stream. The continuous flow spectrophotometer 120 can be substituted by any continuous flow analyzers. Non-limiting examples of continuous flow analyzers that can be used in these embodiments include ReactIR (FTIR) (available from Mettler-Toledo International headquartered in Columbus, Ohio, USA), SEAL continuous segmented flow analyzers (available from SEAL Analytical Limited headquartered in Southampton, United Kingdom), SAN wet chemistry analyzer (available from Skalar Analytical B.V. headquartered in Breda, Netherlands), Shimadzu UV Vis Spectrophotometers (available from Shimadzu Corporation, headquartered in Kyoto, Japan), and Ocean Optics Spectrophotometers (available from Ocean Optics Inc. headquartered in Dunedin, Fla., USA).

A "data analysis engine" refers to one or more software modules that handle data, formulate models and rules, and perform data matching, training and cross-validation by using appropriate logic and criteria, including but not limited to software for automated control of the solvent injection and mixing with the effluent stream. In some embodiments, the data analysis engine can be implemented as part of a server, a user computing device and the like. Examples of suitable implementations of the data analysis engine include servers, authorized user computing devices, smartphones, desktop computers, laptop computers, tablet computers, and other types of processor-controlled devices that receive, process, or transmit digital data.

The data analysis engine 124 is communicatively coupled to the solvent delivery unit 108 and regulates the supply of the solvent or mixtures of solvents to the mixing apparatus 106. For example, the data analysis engine 124 can control the flow regulators of the solvent delivery unit 108 to vary the rate of the solvent injection to accommodate uneven production of oil from the core flooding apparatus 102. During the relatively brief periods of production of a stream of nearly pure crude, the data analysis engine 124 can control the flow regulators of the solvent delivery unit 108 to increase the amount of solvent delivered to the mixing apparatus 106. During the relatively longer periods when the effluent contains only traces of crude oil, the data analysis engine 124 can control the flow regulators of the solvent delivery unit 108 to decrease the amount of solvent delivered to the mixing apparatus 106, and thus the solvent consumption can be significantly reduced. In certain embodiments, the data analysis engine 124 can be communicatively coupled to the coreflooding apparatus 102 to provide more comprehensive data about the hydrocarbon recovery in the core block. In certain embodiments, the data analysis engine 124 can direct the flow of the first stream 116 to one or more pieces of analytical equipment other than a continuous flow spectrophotometer 120. In this embodiment, other analytical equipment can include ultraviolet fluorescence analyzer, infrared fluorescence analyzer, and other visible and UV/visible spectrophotometers.

Embodiments of the system disclosed here also include computer systems, associated with the analytical equipment and the data analysis engine 124, which include a memory, a processor, and one or more input/output (I/O) interfaces. The memory can include non-volatile memory (e.g., flash memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), bulk storage memory (e.g., CD-ROM, DVD-ROM, or hard drives), and combinations thereof. The memory can include a non-transitory computer-readable storage medium having program instructions stored therein. The program instructions can include program modules that are executable by a computer processor to cause the functional operations described here, including those described with regard to determining the maturity of source rock samples.

The processor can be any suitable processor capable of executing/performing program instructions. The processor can include a central processing unit (CPU) that carries out program instructions (e.g., the program instructions for the methods shown in FIG. 2) to perform the arithmetical, logical, and input/output operations described here. The processor can include one or more processors. The I/O interface can provide an interface for communication with one or more I/O devices, such as a joystick, a computer mouse, a keyboard, a display screen (e.g., an electronic display for displaying a graphical user interface (GUI)), a touch or voice responsive device, and the like. The I/O devices can include one or more of the user input devices, one or more data acquisition devices, one or more data processing instruments, and combinations thereof. The I/O interface can provide an interface for communication with one or more external devices, such as other computers, networks, data acquisition devices, sampling devices, and combinations thereof. The I/O devices connected to the I/O interfaces, the analytical equipment, and the data analysis engine 124 are communicatively coupled via a wired or a wireless connection. The devices and equipment include an antenna, a transceiver, and other components required to be communicatively coupled to each other and to the data analysis engine 124. In some embodiments, the external devices include an upstream facility. The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosure.

Figure 2:
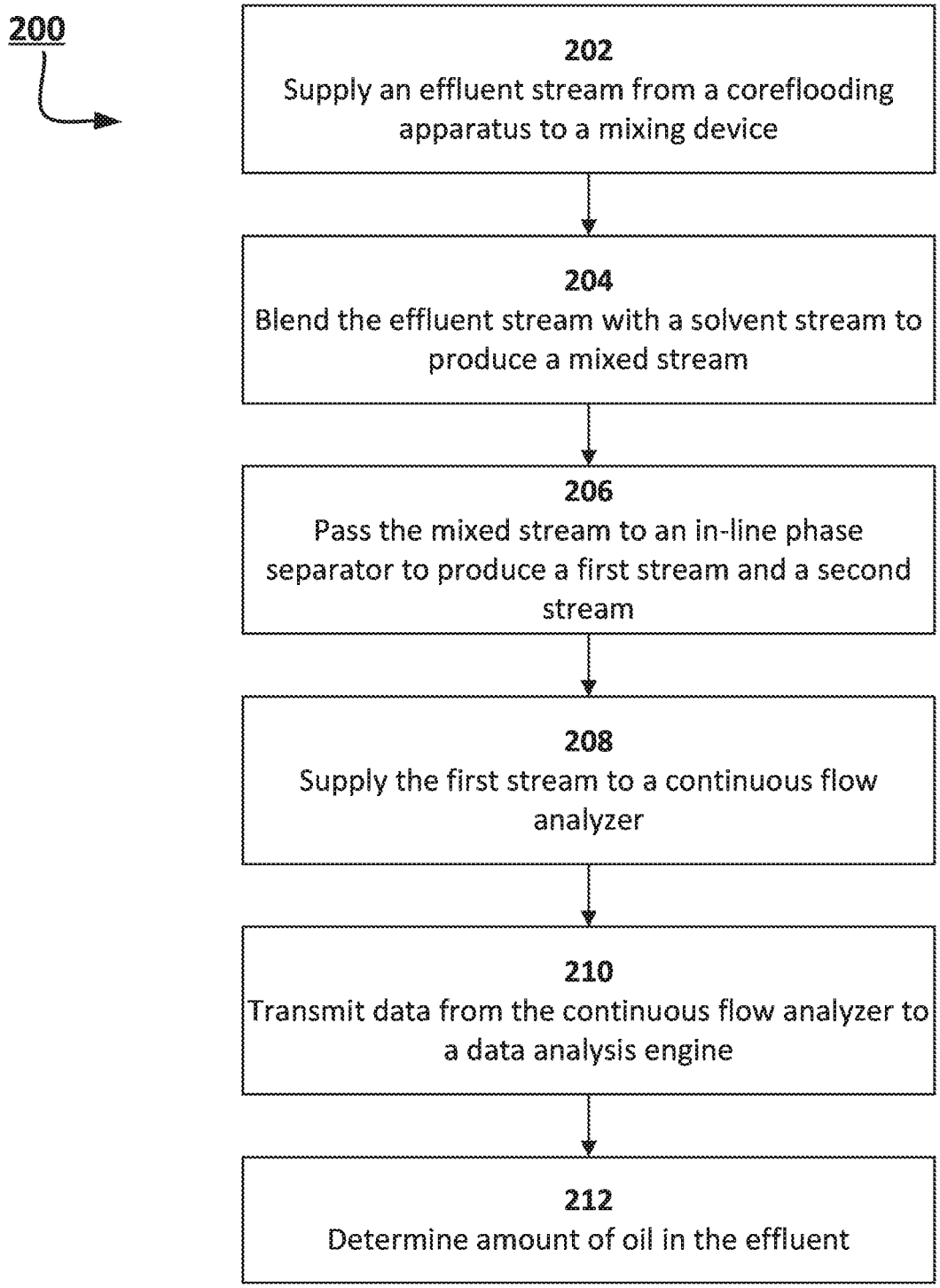
FIG. 2 is a diagram of a method for determining real-time spectrophotometric quantification of crude oil, according to an embodiment.

FIG. 2 is a flowchart of a method for accurate real-time quantification of the amount of oil in a stream possibly containing aqueous, gaseous, or a combination of both phases. In an embodiment, this stream is an effluent stream from a coreflooding test. The method includes the step 202 of supplying an effluent stream from a coreflooding apparatus to a mixing device, the step 204 of mixing a precisely controlled stream of solvent or a mixture of solvents miscible with the oil, but not water with the effluent stream, and the step 206 of passing the mixed stream through an in-line phase separator to produce a first stream and a second stream. The phase separation step can be accomplished by any suitable phase separation device including membrane separators, microfluidic separators, porous media separators and centrifugal separators. In step 208, the first stream containing the solvent and solvent-miscible oil components from the effluent stream is supplied to an analytical equipment such as a continuous flow analyzer. In step 210, data from the continuous flow analyzer is supplied to a data analysis engine, and as shown in step 212, the data analysis engine determines the instantaneous concentration of oil in the solvent stream, and integrates the instantaneous concentration to determine the cumulative amount of oil.

The solvents used in the systems and methods disclosed here may have any specific gravity and be less dense, denser, or have the same density as the aqueous phase. These solvents do not form mixtures with crude oil that lead to deposition of any of components from the effluent stream as a separate phase. For instance, the use of saturated hydrocarbons or mixtures thereof with heavier crudes may result in precipitation of asphaltenes that could clog the equipment or result in inaccurate quantification of crude owing to non-linear relation of optical absorbance of the resulting dispersions to their crude content. Non-limiting examples of solvents include benzene, toluene, xylenes, ethylbenzene, trimethylbenzenes, ethyl acetate, propyl acetate, methyl propionate, dichloromethane, and combinations thereof. In certain embodiments, the solvents used can be toluene, xylenes, or combinations thereof.

In certain embodiments, the solvent stream containing a particular solvent or a mixture of solvents is generated by a suitably accurate pump, such as the pumps used to drive fluid flows through core flooding apparatus or High Performance Liquid Chromatography equipment (HPLC). The rate of the solvent injection can be varied to accommodate highly uneven production of oil from the core flooding apparatus that can include relatively brief periods of production of a stream of nearly pure crude, and much longer periods when the effluent contains only traces of crude. In certain embodiments, during these periods of trace oil production, the solvent injection rate can be significantly reduced to save the solvent. The mixing of the multiphase stream and the solvent stream could be affected by any suitable mixing device including commercially available millifluidic or microfluidic mixers.

In certain embodiments that involve spectrophotometric analysis of the oil effluent from the coreflooding tests, a calibration curve is obtained that is specific to a particular combination of solvent(s) and oil. First an initial wavelength search is done to identify the best wavelength range for obtaining the calibration. This process involves (a) making a series of solutions of a crude oil sample in this solvent or solvents with known concentrations, (b) recording the absorbance spectra of these solutions in the range of 200-1500 nm, or more specifically around 350-800 nm, (c) establishing the spectral range where the slope of the calibration curve (relationship between the absorbance and the concentration of the crude) has least error slope, and (d) selecting a wavelength or a range of wavelengths for absorbance monitoring. In the ideal wavelength range, a linear relationship exists between absorption and concentration according to the Beer-Lambert law.

Development of the calibration curve in the selected spectral range will also provide the range of concentrations of crude in the solvent amenable to spectrophotometric analysis. In this range, the highest absorbance values do not exceed 3 to 4 absorbance units. The selected range of concentrations is used to set the solvent injection rate, so that the solvent-miscible oil components in the oil-phase stream produced by the phase separator are dilute enough for accurate spectrophotometric analysis (absorbance less than 3 units) even if the original mixed phase stream contains only crude oil. Several of the useful attributes of the methods and system disclosed here include a continuous monitoring of oil content in a multiphase stream, a real-time monitoring of oil content in a multiphase stream, an accurate quantification of the oil content, and easy automation of the monitoring to facilitate record-keeping and analysis.

Methods disclosed herein are capable of measuring a range from about 100 ppm volume of crude oil in toluene to about 2,000 ppm volume of crude oil in toluene. Systems and methods disclosed herein can be used to determine oil in oil-containing fluids such as water used in hydrocarbon recovery, coreflood effluent, high water-cut field produced water, or combinations thereof. In certain embodiments, the error rate of the methods disclosed here is less than about 10 volume percent. In certain embodiments, the error rate of the methods disclosed here is less than about 5 volume percent. In certain embodiments, the error rate of the methods disclosed here is less than about 1 volume percent.

EXAMPLE

Figure 3:
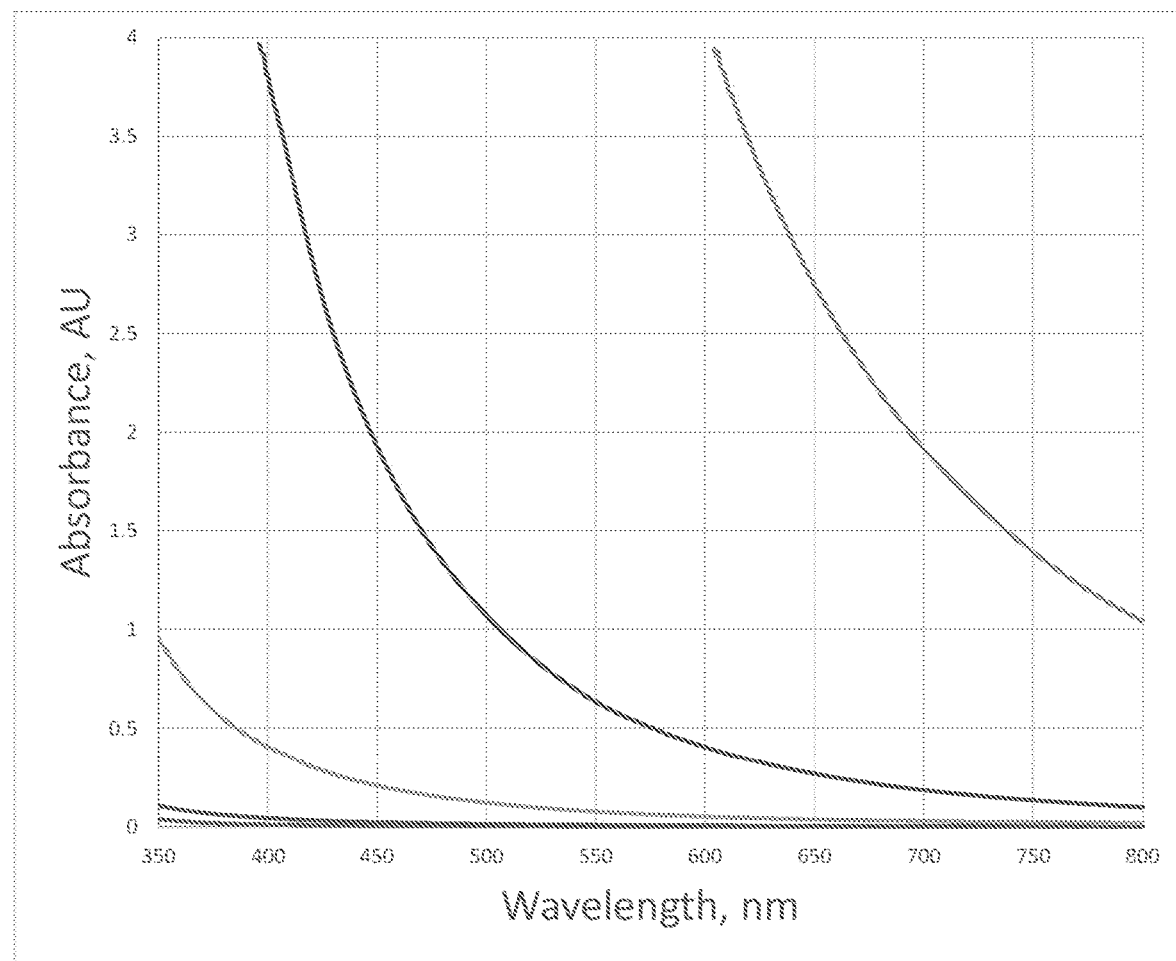
FIG. 3 is a graphical representation of the UV-Visual spectra of a series of known dilutions of Arabian light crude oil in toluene, according to an embodiment.

A series of solutions of the Arabian light crude oil in toluene were prepared and the absorbance spectra of these solutions were recorded in the range of 350-800 nm. FIG. 3 is a graphical representation of the ultraviolet-visual spectra of a series of known dilutions of Arabian light crude oil in toluene, according to an embodiment. The spectral range was established where the slope of the calibration curve (relationship between the absorbance and the concentration of the crude) is determined most reliably. Crude oil samples were diluted in the range of about $4 \times 10^{-2}$ mL to about $4 \times 10^{-6}$ mL of crude in 1 mL of solution. The selected curves are the ones with absorbance in the range of 3-4 absorbance units (dilutions of $4 \times 10^{-3}$, $4 \times 10^{-4}$, $4 \times 10^{-5}$, and $4 \times 10^{-6}$ mL shown as purple, green, red and dark blue lines.)

Figure 4:
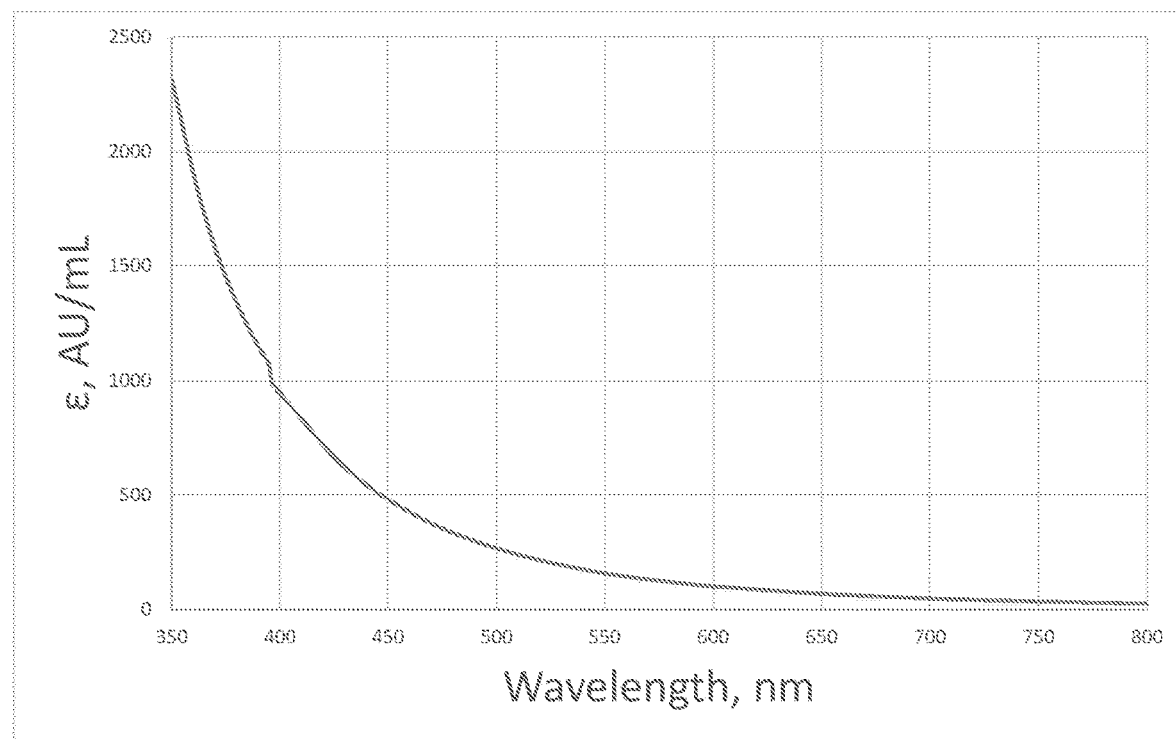
FIG. 4 is a graphical representation of the extinction coefficient of Arabian light crude in toluene, according to an embodiment.
Figure 5:
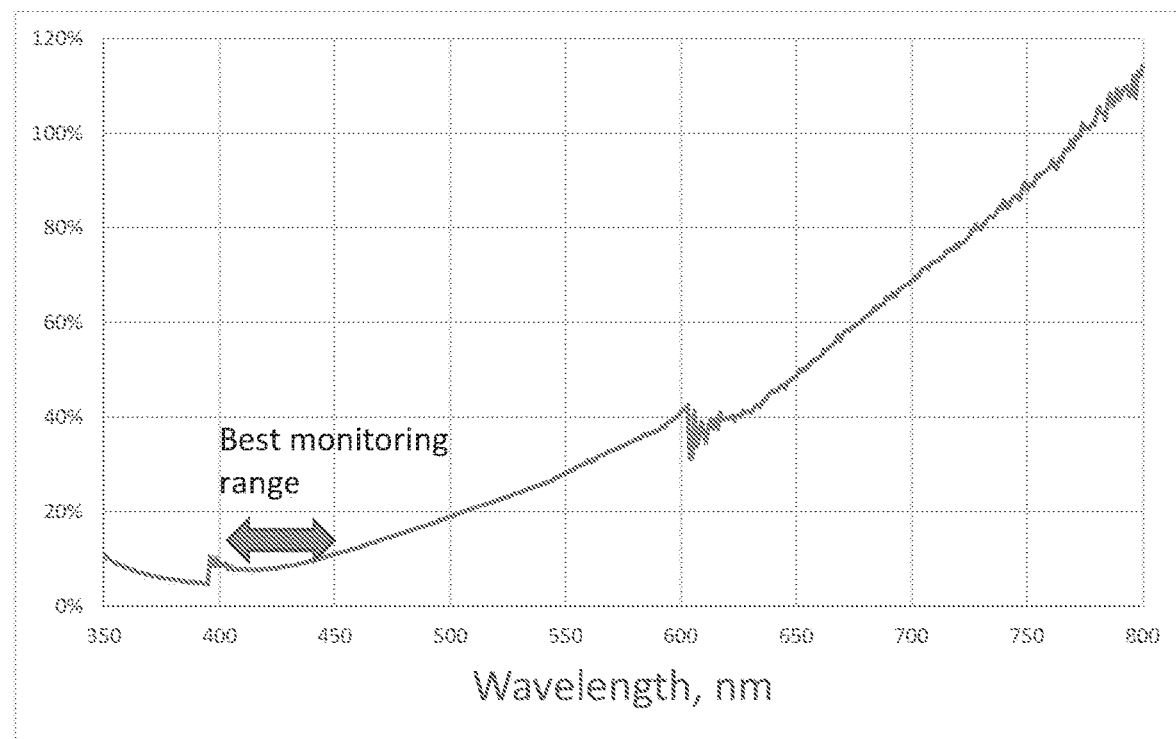
FIG. 5 is a graphical representation of the wavelength range for oil content monitoring from relative width of 95% confidence interval, according to an embodiment.

The extinction coefficient allows for estimation of the molar concentration of a component in the solution from its measured absorbance. FIG. 4 is a graphical representation of the extinction coefficient of Arabian light crude in toluene, according to an embodiment. FIG. 5 is a graphical representation of the wavelength range for oil content monitoring from relative width of 95% confidence interval, according to an embodiment. The 350-400 nm range was rejected because of insufficient data. The calibration curve also provides the range of concentrations of crude in the solvent amenable to spectrophotometric analysis, so that the highest absorbance values do not exceed 4 absorbance units, most preferably 3 absorbance units. The selected concentration range will, in turn, be used to set the solvent injection rate such that the solvent-miscible oil-containing stream produced by the phase separator is dilute enough for accurate spectrophotometric analysis (absorbance less than 3 units). The step of determination of the instantaneous crude concentration in the solvent-miscible oil-containing stream can be effected by any suitable spectrophotometric detector operating in the wavelength range of interest including commercial diode-array detectors supplied by HPLC equipment manufacturers.

Bench top tests were performed with a batch of samples collected in a coreflooding experiments using sample-wise toluene extraction followed by spectrophotometric analysis of the extracts. The resulting oil recovery curve was very smooth with standard deviation of cumulative oil volume of less than 0.5% at every point. The recovery experiment was conducted using carbonate core plugs from Arab-D formation, 1.5 inch in diameter and about 1.98 to 2.41 inches in length, with pore volumes, porosity and permeability ranging from 40 to 45 mL, 22 to 24.5% and 710 to 843 milliDarcy (mD), respectively. Effluent samples were prepared as solutions in toluene (10 mL each). The early samples had collections of about 3.5 to 4 mL (oil and water) and later samples had about 8 mL. The first few oil-toluene samples (20-30) samples were too concentrated for the UV analysis, so they were further diluted by the factor of 100 (or 1000 in some instances) from the original toluene solutions to achieve acceptable absorptivity.

Figure 6:
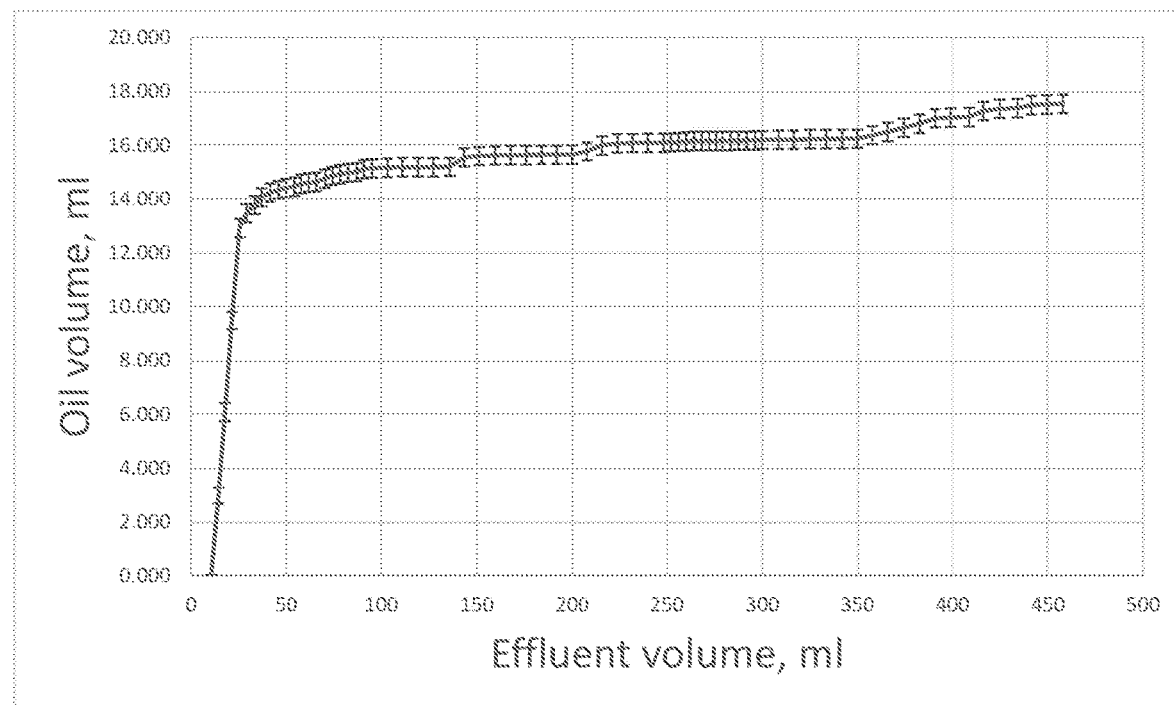
FIG. 6 is a graphical representation of the cumulative oil recovery in a core flooding experiment determined by monitoring 350-800 nm wavelength range, according to an embodiment. Error bars represent 95% confidence interval. The total recovery is 17.59±0.34 mL.
Figure 7:
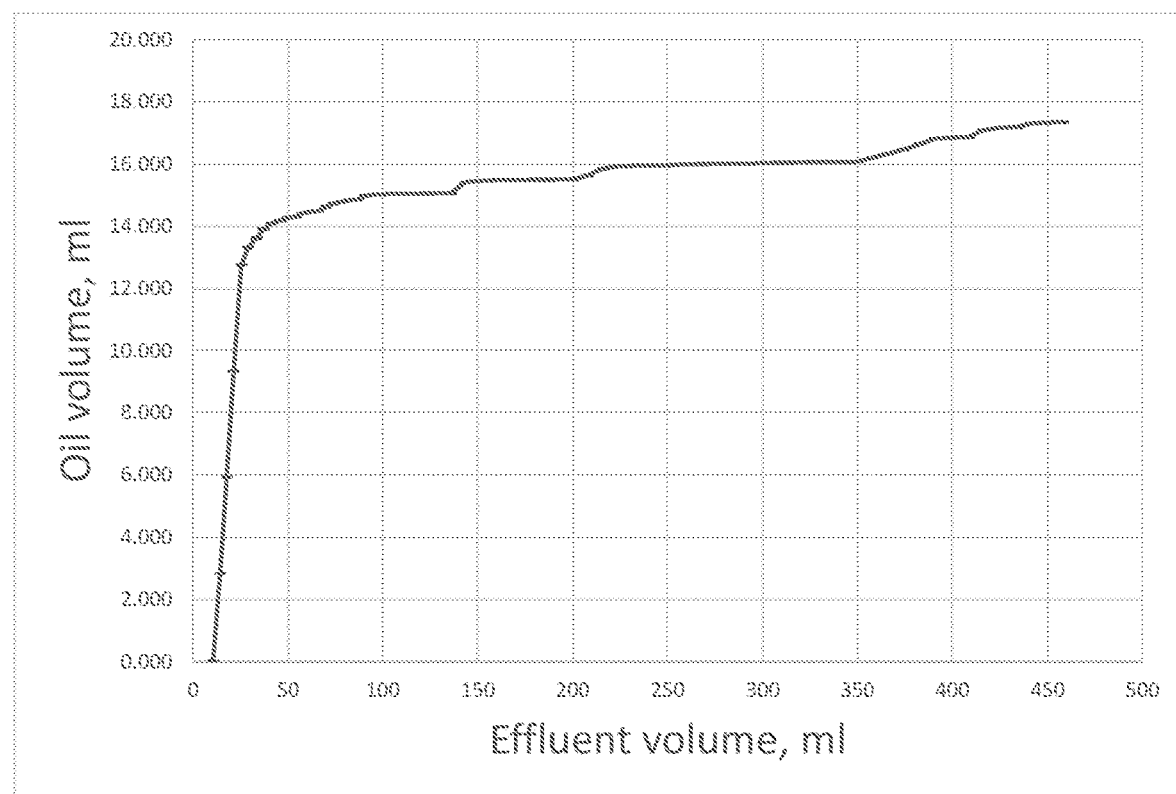
FIG. 7 is a graphical representation of the cumulative oil recovery in a core flooding experiment determined by monitoring 410-450 nm wavelength range, according to an embodiment. The total recovery is 17.38±0.02 mL. The confidence interval is too narrow to be seen.

FIG. 6 is a graphical representation of the cumulative oil recovery in a core flooding experiment determined by monitoring absorption in the 350-800 nm wavelength range, according to an embodiment. Error bars represent 95% confidence interval. The total recovery is 17.59±0.34 mL. FIG. 7 is a graphical representation of the cumulative oil recovery in a core flooding experiment determined by monitoring absorption in the 410-450 nm wavelength range, according to an embodiment. The total recovery is 17.38±0.02 mL. The confidence interval is too narrow to be seen.

Figure 8:
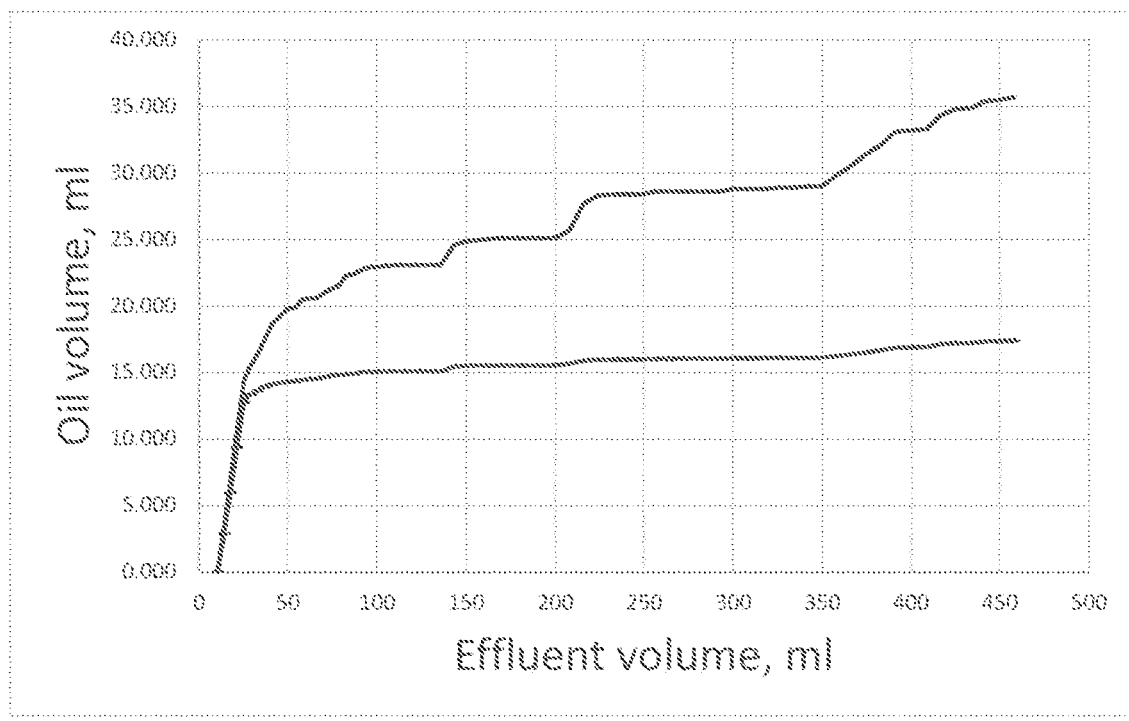
FIG. 8 is a graphical representation of the cumulative recovered oil volume by visual determination in graduated test tubes (red curve) vs. spectrophotometric analysis (blue curve), according to an embodiment.

FIG. 8 is a graphical representation of the cumulative recovered oil volume by visual determination in graduated test tubes (red curve) vs. spectrophotometric analysis (blue curve), according to an embodiment. Fluid level-based methods of monitoring cumulative recovered oil result in data with lots of noise that impede evaluation of temporal aspects of improved or enhanced oil recovery treatments of hydrocarbon formations. Manual sample collection-based methods provide higher accuracy, but are very time-consuming and laborious. Embodiments in this disclosure provide direct real-time precision monitoring of oil content in mixed-phase streams. The high accuracy and vigilant monitoring of samples is made possible in certain embodiments by real-time continuous extraction of oil from the mixed stream followed by continuous analysis, such as by spectrophotometric quantification. The continuous nature of the methods described in these embodiments lends itself to ease of automation.

Further modifications and alternative embodiments of various aspects of the apparatuses and methods disclosed here will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent to one skilled in the art after having the benefit of this description of the embodiments. Changes may be made in the elements described here without departing from the spirit and scope of the embodiments as described in the following claims.

The foregoing descriptions of methods, apparatuses, and results obtained using them are provided merely as illustrative examples. Descriptions of the methods are not intended to require or imply that the steps of the various embodiments must be performed in the order presented. As will be appreciated by one of ordinary skill in the art, the steps in the foregoing embodiments may be performed in any order. Words such as "then" are not intended to limit the order of the steps; these words are simply used to guide the reader through the description of the methods. Many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function. Various modifications to these embodiments will be readily apparent to those skilled in the art, and the generic principles defined here may be applied to other embodiments without departing from the spirit or scope of the disclosure.

What is claimed is:

1. A computer-implemented method of determining amount of crude oil in an effluent from a coreflooding apparatus, the method comprising the steps of:
   supplying an effluent stream obtained from a coreflooding apparatus to a mixing device, the effluent stream containing crude oil and water, and the mixing device being in fluid communication with the coreflooding apparatus;
   blending the effluent stream with a solvent stream in the mixing device to produce a mixed stream;
   supplying the mixed stream to an in-line phase separator to produce a first stream containing the solvent and the crude oil from the effluent stream and a second stream containing water and water-miscible components from the effluent stream, the in-line phase separator being in fluid communication with the mixing device, wherein the in-line phase separators includes one or more of a membrane separator, a microfluidic separator, a porous media separator, or a centrifugal separator;
   passing the first stream to a continuous flow spectrophotometer to determine a plurality of absorption values corresponding to the crude oil content in the first stream, the continuous flow spectrophotometer being in fluid communication with the in-line phase separator; and transmitting the plurality of absorption values to a data analysis engine to determine the amount of crude oil in the effluent stream.

2. The method of claim 1, further comprising the step of:
varying rate of supply of the solvent stream to the mixing device in response to determining the amount of crude oil in the effluent stream.

3. The method of claim 2, wherein the rate of supply of the solvent stream to the mixing device is selected to ensure that the crude oil in the first stream is suitably diluted for analysis in the continuous flow spectrophotometer.

4. The method of claim 1, wherein the solvent is one or more of benzene, toluene, xylenes, ethylbenzene, trimethylbenzenes, ethyl acetate, propyl acetate, methyl propionate, or dichloromethane.

5. The method of claim 1, wherein the solvent is toluene, xylenes, or combinations thereof.

6. The method of claim 1, wherein the mixing device includes one or more of an agitator, a blender, an impeller, a stirrer, or a propeller.

7. The method of claim 1, wherein the continuous flow spectrophotometer is a continuous flow visible spectrophotometer.

8. The method of claim 1, wherein the continuous flow spectrophotometer is a continuous flow ultraviolet/visible spectrophotometer.

9. The method of claim 1, wherein the coreflooding apparatus contains a cylindrical rock sample from a reservoir.

10. A computer-implemented method of determining amount of crude oil in an effluent from a coreflooding apparatus, the method comprising the steps of:
supplying an effluent stream obtained from a coreflooding apparatus to a mixing device, the effluent stream containing crude oil and water, and the mixing device being in fluid communication with the coreflooding apparatus;
blending the effluent stream with a solvent stream in the mixing device to produce a mixed stream, wherein the solvent is one or more of benzene, toluene, xylenes, ethylbenzene, trimethylbenzenes, ethyl acetate, propyl acetate, methyl propionate, or dichloromethane;
supplying the mixed stream to an in-line phase separator to produce a first stream containing the solvent and the crude oil from the effluent stream and a second stream containing water and water-miscible components from the effluent stream, the in-line phase separator being in fluid communication with the mixing device;
passing the first stream to a continuous flow spectrophotometer to determine a plurality of absorption values corresponding to the crude oil content in the first stream, the continuous flow spectrophotometer being in fluid communication with the in-line phase separator; and
transmitting the plurality of absorption values to a data analysis engine to determine the amount of crude oil in the effluent stream.

11. The method of claim 10, further comprising the step of:
varying rate of supply of the solvent stream to the mixing device in response to determining the amount of crude oil in the effluent stream.

12. The method of claim 11, wherein the rate of supply of the solvent stream to the mixing device is selected to ensure that the crude oil in the first stream is suitably diluted for analysis in the continuous flow spectrophotometer.

13. The method of claim 10, wherein the in-line phase separators includes one or more of a membrane separator, a microfluidic separator, a porous media separator, or a centrifugal separator.

14. The method of claim 10, wherein the solvent is toluene, xylenes, or combinations thereof.

15. The method of claim 10, wherein the mixing device includes one or more of an agitator, a blender, an impeller, a stirrer, or a propeller.

16. The method of claim 10, wherein the continuous flow spectrophotometer is a continuous flow visible spectrophotometer.

17. The method of claim 10, wherein the continuous flow spectrophotometer is a continuous flow ultraviolet/visible spectrophotometer.

18. The method of claim 10, wherein the coreflooding apparatus contains a cylindrical rock sample from a reservoir.

19. A computer-implemented method of determining amount of crude oil in an effluent from a coreflooding apparatus, the method comprising the steps of:
supplying an effluent stream obtained from a coreflooding apparatus to a mixing device, the effluent stream containing crude oil and water, and the mixing device being in fluid communication with the coreflooding apparatus;
blending the effluent stream with a solvent stream in the mixing device to produce a mixed stream, wherein the solvent is toluene, xylenes, or combinations thereof;
supplying the mixed stream to an in-line phase separator to produce a first stream containing the solvent and the crude oil from the effluent stream and a second stream containing water and water-miscible components from the effluent stream, the in-line phase separator being in fluid communication with the mixing device;
passing the first stream to a continuous flow spectrophotometer to determine a plurality of absorption values corresponding to the crude oil content in the first stream, the continuous flow spectrophotometer being in fluid communication with the in-line phase separator; and
transmitting the plurality of absorption values to a data analysis engine to determine the amount of crude oil in the effluent stream.

20. The method of claim 19, further comprising the step of:
varying rate of supply of the solvent stream to the mixing device in response to determining the amount of crude oil in the effluent stream.

21. The method of claim 20, wherein the rate of supply of the solvent stream to the mixing device is selected to ensure that the crude oil in the first stream is suitably diluted for analysis in the continuous flow spectrophotometer.

22. The method of claim 19, wherein the in-line phase separators includes one or more of a membrane separator, a microfluidic separator, a porous media separator, or a centrifugal separator.

23. The method of claim 19, wherein the mixing device includes one or more of an agitator, a blender, an impeller, a stirrer, or a propeller.

24. The method of claim 19, wherein the continuous flow spectrophotometer is a continuous flow visible spectrophotometer.

25. The method of claim 19, wherein the continuous flow spectrophotometer is a continuous flow ultraviolet/visible spectrophotometer.

26. The method of claim 19, wherein the coreflooding apparatus contains a cylindrical rock sample from a reservoir.

* * * * *